United States Patent
Birkeland et al.

(10) Patent No.: US 7,087,410 B2
(45) Date of Patent: Aug. 8, 2006

(54) **SYSTEMS FOR EXPRESSION OF HETEROLOGOUS PROTEINS IN *M. CAPSULATUS***

(76) Inventors: Nils Kåre Birkeland, Vågeladen 34, N-5162 Laksevåg (NO); Ingvar Eidhammer, Kleivadalen 47, N-5261 Indre Arna (NO); Inge Jonassen, Midtunhaugen 84 D, N-5224 Nesttun (NO); Harald B. Jensen, Vollane 13, N-5105 Eidsvåg (NO); Torleiv Lien, Måsekjaerveien 10, N-5035 Bergen (NO); Johan R. Lillehaug, Ibsensgt. 89, N-5052 Bergen (NO); Ivar Lossius, Nye Sandviksvei 80, N-5035 Bergen (NO); Jonathan A. Eisen, 662 Lake Varuna Mews, Gaithersburg, MD (US) 20875; Claire M. Fraser, 11210 S. Glen Rd., Potomac, MD (US) 20854; A. Scott Durkin, 18061 Cottage Garden Dr. #103, Germantown, MD (US) 20874; Steven L. Salzberg, 147 Little Quarry Rd., Gaithersburg, MD (US) 20878

( * ) Notice: Subject to any disclaimer, the term of this patent is extended or adjusted under 35 U.S.C. 154(b) by 121 days.

(21) Appl. No.: 10/466,196

(22) PCT Filed: Jan. 14, 2002

(86) PCT No.: PCT/NO02/00018

§ 371 (c)(1),
(2), (4) Date: Jul. 11, 2003

(87) PCT Pub. No.: WO02/055549

PCT Pub. Date: Jul. 18, 2002

(65) Prior Publication Data

US 2004/0175705 A1    Sep. 9, 2004

(30) Foreign Application Priority Data

Jan. 12, 2001 (NO) .................................. 20010238

(51) Int. Cl.
C12P 21/04 (2006.01)

(52) U.S. Cl. .................. 435/69.7; 536/23.7; 536/24.1; 536/24.2; 435/320.1; 435/69.1; 435/243; 435/252.3; 530/350; 424/234.1; 424/192.1; 424/193.1

(58) Field of Classification Search ............... 536/23.7, 536/24.1, 24.2; 435/320.1, 69.1, 69.7, 243, 435/252.3; 530/350; 424/234.1, 192.1, 424/193.1
See application file for complete search history.

(56) References Cited

OTHER PUBLICATIONS

Zhuang et al., "*Caulobacter* FliQ and FliR Membrane Proteins, Required for Flagellar Biogenesis and Cell Division, Belong to a Family of Virulence Factor Export Proteins," Journal of Bacteriology 1995; 177: 343-356.

Loosmore et al., "Outer Membrane Protein D15 Is Conserved among *Haemophilus influenzae* Species and May Represent a Universal Protective Antigen against Invasive Disease," Infection and Immunity 1997; 65(9): 3701-3707.

Georgiou et al., "Display of heterologous proteins on the surface of microorganisms: From the screening of combinatorial libraries to live recombinant vaccines," Nature Biotechnology 1997; 15: 29-34.

Fjellbirkeland et al., "Outer membrane proteins of *Methylococcus capsulatus* (Bath)," Arch Microbiol 1997; 168: 128-135.

Fjellbirkeland et al., "Molecular analysis of an outer membrane protein, MopB, of *Methylcoccus capsulatus* (Bath) and structural comparisons with proteins of the OmpA family," Arch Microbiol 2000; 173: 346-351.

Fjellbirkeland et al., "The C-terminal part of the surface-associated protein MopE of the methanotroph *Methylcoccus capsulatus* (Bath) is secreted into the growth medium," Arch Microbiol 2001; 176: 197-203, Sep. 2001.

International Search Report for PCT Application No. PCT/NO02/00018 issued by the Swedish Patent Office on Jun. 25, 2002.

*Primary Examiner*—Jennifer E. Graser
(74) *Attorney, Agent, or Firm*—Reed Smith, LLP

(57) ABSTRACT

The present invention relates to an expression system for the expression of proteins and peptides in a methanotrophic bacterium, preferable the *M. capsulatus*. Further, the invention relates to the exportation and display of said peptides and proteins on the surface of said bacteria. The invention also describes a method for the production of a desired protein in the *M. capsulatus*.

38 Claims, 5 Drawing Sheets

SEQUENCE LISTING

<160> NUMBER OF SEQ ID NOS: 14

<210> SEQ ID NO 1
<211> LENGTH: 1496
<212> TYPE: DNA
<213> ORGANISM: Methylococcus capsulatus

<400> SEQUENCE: 1

```
gatcagagcc ggttcggcag gttgtcgttg accaccggca cgcggcagtt gtccagagac      60
aggccgggcg catggctgta gggcaggatc ggattgttgg gatcgaactt gccatccgcc     120
gacggggtgt tgcccgccgt ggtcaccgcg agataaccgc cctggccgaa gggatgcgcg     180
taggcggcgt tgttcttggc ggtcaggctg gggctgccgg catcggatgc gatcttctgg     240
atgatcttca gcttgtcgcc ggtcggaccg ttgtaggcgg gtttgcgcca ttgataggta     300
ttttccgccc aatccatgta gtggccgctt gccgtgttgg cgagcgtggg tgcaacgccg     360
tcgatggcga tgaaacggta gttgtatttg aggttggcat tgcgttcggt gctctgtaca     420
ccgatggccc aggccttgac tccggccgca ttggctttgc tgttgttggt gccttgattg     480
```

```
aaatcatcca ggcaggtgtc gacattcccc gcgcccgagt tcaggatcac gaccggtcct      540
gccagcggat tggaggtgga agcgggactc aatgcgctgt cggtgcaggg tgcattgagg      600
aaattggcat tggtggtggc ctgggtaccg atccgttga cccggcggca gatatagacc       660
ttgtcgtccg tgatcgatcc gttggcgtat tgggtcaagt cgcctttcgc ctggccgttc     720
ttgtcgacga ctttgatttc gctccatttg ccgatgttgc cggtgagcag gctggcgatc     780
tgatactttc tcaggctggg catgcagcgc tcggtgtcct gcccttcgca gtccgggtcc     840
agggtaccca tgtcgatctg gcgcgctgc aaggcgtcgc gcagagattt ggtcaccggc       900
gtgttgaaaa ccagggcgcc gccggagacc acgtccaggc gctggctgac cttcgcggga     960
tccaccggag ccacgccatc cggcgtgttc atgctccgga acatcgcggg attgacgtcg     1020
gagacgccgc cgtcggacac cttttgcgcg aggtcgccgg gctgggagat ccggcacagc     1080
cagttaccgc tcgccgcatc cttctggcag ttgccgttgt tgatcatcat ggcgtcgatc     1140
gcctgttcgt cgagcaccgg gcccacaccc tgcgccgaac cgccggcgga gcgcttgtgg     1200
aacagtactt tgggattgtt gacggaaagc cccgtcactt tggacgaatc gatctggcag     1260
aagatagccg tgtgtgcgga accggggttg gaggggttcg agttgtcgaa atagacatcg     1320
agcgttcctc ccacgcagag ttcttcgaac aattgccgga cattgccatc ctgggccgat    1380
gcgccggaca tgaagatttc gatgtcgggc gatacgccgg gttccaatgc ccagccctga     1440
gcgcagaatc ccagagagct tgccgcgacc gctgcagcga ttttcttgac ttgcat        1496

<210> SEQ ID NO 2
<211> LENGTH: 1374
<212> TYPE: DNA
<213> ORGANISM: Methylococcus capsulatus

<400> SEQUENCE: 2
atgcatcgcc catgtctgaa tccggccggc tcggcaacgc cgggttcgcg tggcgaacga      60 gagttttttcc catttacgga gagtgcgaaa accatgaaga aattgcgagc agttttttctg    120 ggcacgctgg tcgccgcggg gcacccggcc catgcggcca tcaacgacgg gaagttcgga     180
acgccgggcg agttgttcat ctcgatcctg gatgtggacg gaaagaagtc ctattacaag    240
gacctcggcg tcgatatggt ccagttcatg aacggccagg gctgcctcga cgccaatctg    300
gcgcaggatc ccaattttgc ggcctttgcc ggcaaaacca acctggtcta caacatcgcg    360
gcggtcaatc ccttgctgaa ggatgccagt aacatcactc aatggggcta tctggccaca    420
tcgagccagg gcaaggacat tttcagcgcc aaatggaact tgatcgacaa tgcgatccag    480
aagatccagg gttacatcgc cgccctcaac gtccagccgt tcgagaacaa gcccgggcag    540
gcggcggaga acaaatcggg cgtgttcggt cccgacgacc ttgcctatca cggcaagggc     600
acctggggtc ccaccatggg aagctccgtc aacggcaaca ccgaaggtgc cccggcgcc     660 gaactcgagt tctatttcgt caacaactcc accggcgatt ccaaggggga acacatcacg     720
aagctggggg catggagctt gtcgagcgcc ggcgctctga gctacagcgg caccggcacc    780
tcgaccctgt gctcgggatc ggggaacaaa gccccgacgg cggccatcac caatcccgct    840
cagacggtag cggtcaatac caccgtcacc ctggacggca gcgccagcac cgatcccgac    900
aacggtcccc aacccttgtc ctacgcatgg aagcagacct ccggcccac ggtgacgttg      960 agcaacgctg atcaggcgaa agccagcttc acacccgccg aggtcggcag ctacaccttc    1020
cagttgacgg tcagcgacgg cgccgccacc ggtaccgccc aagccaccgt cacgggtggaa    1080 ggcagctcca cgggcgcttc catccacatc gatgcgcccg cggcctggaa ggtcaagcag    1140
```

```
gctcagacag tcgcctggac caccacggaa gtgccggcca gcaagctggt caacctcgag    1200
ttctccaccg acggcggctc caagttcaag aaactgaaga gcgtcgccaa caaaaaagga    1260
cagaccctgt ggaaaccgac caagaagcac gtcacacaac agggtgtgct ccgggtttgc    1320
gtcaaaccga gcaaaaagtt ctcgttcgtc tgcgaccaga tcgacgtcac gggg          1374

<210> SEQ ID NO 3
<211> LENGTH: 1624
<212> TYPE: DNA
<213> ORGANISM: Methylococcus capsulatus

<400> SEQUENCE: 3
atgagagaca ccatgaacga aaagcattgc tactccttac tggccgccgg cctcatcgcc      60
gccgtgccgc aactcgcagc cgcccacgga ggcactcacg acgtcaccgc ggtcgcccac    120
ctgagctatt cggaagccta ttcggaaaag ctcaagaagg gtcaggaagt gggcaccgag    180
ctgctggtgc tggacggacg cttcgaattc aacgaacacg tcggcatggg tgacatcacc    240
ccggacacga cctggtcggc cgtcgtgcag ggccagaccc tggcaacggg taccctgggc    300
gacgccacca agaagaagtt cggcgccaag ggcggcatgg cggtgatcaa cgtgcccggc    360
ggcggtacgc tcaaattcac ctggaacgcc aaggccatca tgctcaagct gaaatggacc    420
ggcgagccgg ccttggcccg gctgtacaag gaccagaaca ccagcatcaa tctgccgcaa    480
ttcccggtcg acatcgcgat cggcagtctg cacggctact tcaacgttcc ggtcaccggc    540
caggcgaagg ccacgaccaa gaacggcacc atgctgtcca gatcgccctt gaaaggcaca    600
gcgaactccg cgggcctgga cacgctggac cgggacggcg acggctccac ggccgacgcc    660
gattgcaacg acttcgcgcc caccatccat ccgggcgccg ccgaagcgac gctggacggc    720
gtggattcca actgcgacgg cgcgactcc ggcgtggcgg aagtcgtcga gaccttcaag    780
aatccgggca cctactccag cccggtcatc aacttcaaga tcgcttcgcc gccggggccg    840
ggaacgccca tctacgggcc gccgcgtgat ttctccggtt acaacaagag ctactcgctg    900
gcgatcggca gacctcgta ctacgatccg accaccggca ccaagtggaa cgacgacacc     960
atcacgccgg tcagtgatgg tcaggacatc tggcgcggct ggacccatac cggcaagtgg    1020
tcgttcttca acggcaaggc cggcgacaag atcaccctca gcgtacagcg tgatgcgcag    1080
gaagccagcc tgaaaggcgc ccatccgggc ttcatcctgt tctggcggcc cgagggcggt    1140
ccgctgttct gggccggcac ccaggatctc gacgagggcc agaccgcgct gcccgccgac    1200
tccgacaccg ttatcggcca cgtgatcgtt cagcacgccg actggaccct gcagggcttg    1260
ccgcccaagg ccgaccatac cgcacccgcg ggcgtggata ccgagctcta tcccatgaag    1320
ccggacagct acaccatgta ctacgtcgac tccggctacg atgccgacaa gtacgtggca    1380
tcgaagaagc tcatcatgca ccccacggcg ttcaaagggc tggccctgaa cgacggcacc    1440 gccgggcgt tcaccaagtc catcaccctg ccgaagacgg gctattacat gctgtacgtc    1500
gccaacgtcc tggaagtgga cgactggagc gtcgacgcgg acggcaagct caccaccacc    1560
ggcgaagtct ggraagtgcc ggccaagggc tgctgggtca acatcacgat ctccaagccg    1620
taaa                                                                    1624

<210> SEQ ID NO 4
<211> LENGTH: 842
<212> TYPE: DNA
<213> ORGANISM: Methylococcus capsulatus
```

```
<400> SEQUENCE: 4
gccgctccga aagcccatgc ttcttcggcc caggcttcgc tggaacggag actgcaggta      60
atggaacagg aaatgcaggc gctgcgtgct gaactcgagg cgtcgcgctc aaaggccgaa     120
gcggaagcgg cggaagccaa agcggaggca aggatacgct ctcagcaggt acaggctcag     180
caggcgaaag tgaatcaggg gcttgccgag ctggccaaac acgaagaaaa gaaggatgac     240
atggtcttct tccgtggtgg ctgggcagcc atgaatcatg ctcgtaccag cgaactgctg     300
gtcaacaaca atctcctttc gtcgaacaat ttcggttccg acaaggccgg ctggtatgtc     360
ggcgcaggtc tggatcaccg tctgagcgac gacaccttcg gcatttccga cgacctggcg     420
ctcgatgccg aaatcatgtt cgactacaag aactacggca gcgtcaacaa ctcattcgtc     480
agcagcgtga cgggcacgcg gatgcaggcg caggtcacca tgttctcccct gtatgcatct     540 cccaagctga atacaccgg catcgaagga ttccgtccct ggatcgtgcc gttcggtctc     600
agcgtcaacg tcatcagccc gccctccagc ggcgtgaccg tgttgaatcc cggtctgatg     660
ctcggtaccg gtctggagta caatatcttc aagaacctgt gggtgggtgc cgacttccgg     720
tacaacttca ccggcggcga cctgaactac agcgtcagga cgaacaacgg caagaccatc     780
ttgaacagca ccgatacgga caactacacc gccggtgctt acgtcggcat cggcttctga     840
ag                                                                   842

<210> SEQ ID NO 5
<211> LENGTH: 2388
<212> TYPE: DNA
<213> ORGANISM: Methylococcus capsulatus

<400> SEQUENCE: 5
atgaccgacg ggttccggac ttacgcatgc cccatcccat cgcttccggc caggcccttg      60
aacgatagtt ctgccgcatt ttcagggga gtggaatccg tgcgccgcct gtgtgcatgg     120
ttgctgatcc tgacatggtc gtccgtgctg ttcgcgttcg agcccttcgt catccgggac     180
atccggatcg agggctgca gcggatttcg gagggtacgg tgttcaacta cctgcctgtc     240
cgggagggcg acaccctcga tgaaaaacgg tcggccgagg tgatccgggc gctgttcaag     300
acggggtttt tcaaggacgt ccgtctggac gaggacgacg gtaagttgat catctacgtc     360
gaagagcgtc cttcgatttc cagcgtaaag atcgacggca accatgacat cggtagcgag     420
gatctgctga aggcgctcaa gggaatcggg ctggcggagg ggaaggtatt cgaccggcag     480
attctcgaca aggtcgaaca ggaactgcgg cgccagtatt acagccgggg caaatacagc     540
cttaaaatcg attcccaggt gacgaactg ccccggaacc gtgtggcggt gaatatcaat     600
atcgcggagg ggcgcgttgc tcgcataaaa cagatcaata tcatcggaaa taatgcattt     660
agtgatgatg atctgaccca ggattttgag ctgagtacat ccaatctcct gtctttctat     720
accaaggatg atcagtattc caagcagaaa ttgtcggccg atctggagcg gctgcgctcc     780
tactatctcg atcgcggtta cgtcaatttc gaaatcgagt ccacccaggt atcgatcacg     840
cccaacaaga aagaaatata tatcaccatc aacgttaagg agggcgaggt cttcaaggtg     900
gagcaggtca ggctgaccgg caagaccatc gtgccaccccg aacaactcgt cccgctcgtg     960
cgtatcgggc cggaggatat ttttccagg aaactggcga cagaacccca gaagggcatt    1020
tccgatcgtt tgggcgagga gggctatatc ttcgccaacg tcaatatggt gccggacatc    1080
aatcaggaga agaagaccgt aaacatcacc ttttcgtcg atccgggcaa acaggtctac    1140
gtgaggcgaa tcaatttcca gggcaatacc aagacgcgtg acgaagtgct gcgcagggaa    1200
```

```
atgcggcaga tggaggcggc ctgggcgtcg accgcgaaga tcgagcgttc caagaccagg   1260
ctcgagcgtc tcggctattt ccaggatgtc aacgtggaga cgcccgcggt gccgggaacg   1320
acggatcaga tcgacgtcaa ctacagtgtg accgagaagt cttccggcaa cctgacggcg   1380
ggtgtagggt attcccagtt ccagggcatc atattcaatg cggcggtcac ccaggacaac   1440
attttcggca gcggcaagcg tgtcagtttc aatttcaaca acagccagat caacaccatc   1500
tatgccttgg ggtatttcaa tccttacgcc accctggatg gcatcagcag tggtttcgac   1560
atcagctatc gcgacaccaa caccggctat tcgaactatg ttgccaacta cattaccaat   1620
gtgttccagg tgggcggcaa ctgggggttg cccatcggag agttcgacag tattcggacc   1680
aacctggact acagtaacac caagctcaag acgacctccc agtcttccga tcaaatcaga   1740
gcgttcattg ccgaccatgg cagcgagtat tcgacctatt cgtcctcact gggttggacc   1800
catgacaccc tgaatcgggc gatattcgcg accagcggtg gcgcgcagcg attgacggga   1860
ctgtttgccc tgccgttcag caccctgcag tattacaagg ccaacgtgcg cctggagcag   1920
tattttccgc tgacccagga tctgacgctg tggttgaatg cgatttcgg ttacggcggc   1980 ggctatggca gtggcggcaa cagcgtcctt ccgttctggg aacactttta cgccggcggt   2040
ccgaattccg tgcgtggata ccagcccaat tcactgggc ccaggacag ccgtggctac   2100 gccttcggcg caacagcaa actgaccggc tcggtggagt tgctgtttcc ggtcccgttt   2160
gcgggcgaga aactgaagag tgtccgcttg ggtaccttcg tcgacggcgg gaatgtgttc   2220
gtcaattcgc cccagctttc ggacctgcgc ttctcgaccg gcatttcggc caagtggcta   2280
tcacccttcg gggccctgat gttctcgatc gcccagccgc tcaactccca gagcggggac   2340
cgaattcagc attttcaatt caatttcggt tccggattcc agggcatg              2388

<210> SEQ ID NO 6
<211> LENGTH: 1158
<212> TYPE: DNA
<213> ORGANISM: Methylococcus capsulatus

<400> SEQUENCE: 6
ttgccggctc ctcgtggaaa gaaccggatc gcccctcgac cccgaccacc ggctcgctgc     60
cgatcggcca cggtctggca tcggcggggg gagcggtggg aggcgttagg ccggcacggg    120
tggaccctct gccggcgggg tcgcgcccgg acagtggctt cggcagtggt ttcgacggaa    180
ggacgacagg ccacgaaccc ttgcctgcca gcccgacat ttcgcccgac ccacttgaag     240
caggttttcc gcgctcactt gtcaatcccg agagcccgaa aatccacgga tgaccgattt    300
tatgaaggta ttgatctcgg tgttgccgac gcgcgcatag acgtggggtc ggtctgcaca    360 ccctccccc cagctgacga cgccgacttg aatgaccttt cccgagaccc ttcggaacaa     420
cggaccaccg ctgtcgcctt gacaggcgcc cttggcacga acggcggcac acagttgaac    480
agtgccgtcg aacttggaac cgtaggccgt gatatcgcaa agcgcatctt ccatgatggg    540
catggaaact ggcgcatttt ctgccgggaa ataggggggt ggaatgtgat cgtcgttcca    600
ataccaggcg acgatactgc cccatcccgc gaccgtgacc catgtgttgg cgctgtcctg    660
ccctgcggtc gccagccgga cggtcttggc gcgcgccacc ttgcgatcga gttcgagcac    720
ggcgacatca taaggaagcc tgacatcccc gggttccctg tatttcggat gcacatgaat    780
cgccgaaacg cgccgtgctc gtccttgatg ccttccgtag gtcgtcatac cgaccatggc    840
cgtataatcc gacggatcgt tgacgacata cccgccatca tcaagatttt cagtgacaca    900
```

-continued

| | |
|---|---|
| gtgggcggcc gtcaaaacat gacgagagga aatcatactc cctccgcaca catgaccgta | 960 |
| cggatcggac tcggattttc gcgactcccg ctgaagcgcc acgacgaagc cataacgccc | 1020 |
| ttcaaccacc ggatcaccat tgaccacctc aggtctcatc gccagattcc aggcagtctc | 1080 |
| cgccgcctcg gaaccggcgc tcacgagaga tatgcacgac acaacgatcg accatccgcc | 1140 |
| acaccaccgc agcctcat | 1158 |

<210> SEQ ID NO 7
<211> LENGTH: 795
<212> TYPE: DNA
<213> ORGANISM: Methylococcus capsulatus

<400> SEQUENCE: 7

| | |
|---|---|
| atgagacctg aggtggtcaa tggtgatccg gtggttgaag ggcgttatgg cttcgtcgtg | 60 |
| gcgcttcagc gggagtcgcg aaaatccgag tccgatccgt acggtcatgt gtgcggaggg | 120 |
| agtatgattt cctctcgtca tgttttgacg gccgcccact gtgtcactga aaatcttgat | 180 |
| gatggcgggt atgtcgtcaa cgatccgtcg gattatacgg ccatggtcgg tatgacgacc | 240 |
| tacgaaggc atcaaggacg agcacggcgc gtttcggcga ttcatgtgca tccgaaatac | 300 |
| agggaacccg gggatgtcag gcttccttat gatgtcgccg tgctcgaact cgatcgcaag | 360 |
| gtggcgcgcg ccaagaccgt ccggctggcc accgcagggc aggacagcgc caacacatgg | 420 |
| gtcacggtcg cgggatgggg cagtatcgtc gcctggtatt ggaacgacga tcacattcca | 480 |
| cccccctatt tcccggcaga aatgcgccaa gtttccatgc ccatcatgga agatgcgctt | 540 |
| tgcgatatca cggcctacgg ttccaagttc gacggcactg ttcaactgtg tgccgccgtt | 600 |
| cgtgccaagg gcgcctgtca aggcgacagc ggtggtccgt tgttccgaag ggtctcggga | 660 |
| aaggtcattc aagtcggcgt cgtcagctgg ggggaggggg tgcagaccg acccaccgtc | 720 |
| tatgcgcgcg tcggcaacac cgagatcaat accttcataa aatcggtcat ccgtggatt | 780 |
| tcgggctctc gggat | 795 |

<210> SEQ ID NO 8
<211> LENGTH: 2532
<212> TYPE: DNA
<213> ORGANISM: Methylococcus capsulatus

<400> SEQUENCE: 8

| | |
|---|---|
| gtgcgggatt atcggcgcaa tcggaccggc tgtcacggac gatgggcccg attgcagcag | 60 |
| ccgccggttt ggcggatcat gagccctccc gcagttcgtc gacaacaagg aatcatgaac | 120 |
| ggccatcccg ctgcgctccc ccccgaccgt ctccttaccc cctgcgatcc cgccagcttc | 180 |
| tggttcgaaa ccaccgccga actggcggat accgacatca tcatcggcca gccccgcgcc | 240 |
| ctggaagcca tccagctggg cctcaaagtc gctcagaaag ggttcaacgt gttcgtgctg | 300 |
| gggccgcccg gcagcggcaa actgaccgcg gcgcgcgaac tcgcagaacg catcgccgcc | 360 |
| acccagccac cgccgagcga ctggtgctac gtcaacaact tcgccaaccc cgcccagccc | 420 |
| aaggcactgc gcctgccggc cggctgggga cggcacttgg cgcacgacat ggaagtggtg | 480 |
| gtcgaggatc tggtttccgc cctccggca gccttcgaag gcgaggaata ccgcagccgc | 540 |
| gccgaaaaga tcgaacagca ggcgcgcgag cgcgaagccg aggcggtcaa ccggctacgg | 600 |
| gcggaggcat tgcggagccg catcgcactg atcgagaccc cgaccggctt tgccttcgct | 660 |
| ccgatgcagc gggaccagga cgagatcatc agcccggacc agttccagaa cctgtcggac | 720 |
| caggaacgcc aggccatcga gaccaccgtc gccgacctgc agcagcaact gcagaagatc | 780 |

```
ctccgccagt tccggcctg gcgcaaagag gcgcgcggca aactcaaggc gctcaaccgc      840
gaaatcgccg aattcacggt gtcccatcag ttcgccgacc tcaaagcacg ctatgccagc      900
ctgcccggcg tgatcgagta cctgaacctg gcccaggccg acatcatcga acacacagag      960
tcgtttctcc ccaaggccga aggcgtcatc agcctgttcg aagggccgca gaaagcgccg     1020
gcacagcgct accggatcaa cctggtggtc gatcacagcg aactcaccgc cgcaccggtg     1080
gtgcaggaag atctgcccac ccacggcaac ctgatcgggc ggatcgagca ccaggcccac     1140
atgggagcgc tggtgaccga tttcaccatg atccggccgg gcgccctgca caaagccaac     1200
ggtggctacc tgctgctcga tgcgcgcaaa ctcctgagcc agccgttcgc ctgggagacg     1260
ctgaagcgcg ccctgcatgc cggcgagatc cgcatcgaag cgctggaacg cagcctcagc     1320
ctcatcagta ccaccagcct ggaaccggag ccgatcccgc tggatctcaa ggtcatcctg     1380
ttcggcgagc gcatgctcta tttcctgctg acatctatg accggaatt ccccgagttc      1440
ttcaagatcg ccgccgactt cgaagaggtc ctgccacgcg acgcggattc gatcgaactg     1500
tacgcgcgga tggttgccac cctggcccgc cgcgagaaac tgcggccgtt gcaccgggag     1560
gcggtggccc gcatcgtcga gcatgcctcg cggcggaccg gcgacagcga gaagctgagc     1620
gcgcatctgc gcagtctggc cgacctgatg agggaggccg atttctatgc aggcagcgac     1680
ggacgcaacc tcatcaccgc agccgacgtc gaacacgcca tcagccgccg gatctaccgc     1740
tccgaccgcc tccgcaaccg ggtccaggaa gcgatacggc gggggctgat cttcgttgac     1800
accgaaggtg cggtagcggg ccagatcaac ggcctctccg tattccagct caatgatttc     1860
gccttcggcc agccctcgcg gatcaccgcc accaccccgtc ccggcagcgg acgcatcctg     1920
gacatcgaaa agaaaccga gctcggcggc gccctgcaca gcaaaggcgt gctgatcctc     1980
ggcaatttcc tcgcttcgcg ctattccggc gcccagggct tctcggtcgc cgccagcctg     2040
gtgttcgagc agtcttacgg cggcgtggac ggcgacagcg cttcgctggc cgagctgtgc     2100
gcggtgctgt cctcgatcgc cgaagtgccg atccggcaga gtctggccat caccggttcg     2160
gtcgaccagc acgccgggt gcagcccata ggcggcgtga acgagaagat cgaaggcttc     2220
ttcgacgtct gcgcggcgcg cggcctgacc ggcgaccacg gcgtgatcat cccggcggcc     2280
aacgtcgtgc acctgatgct gcggcgggac gtggtgcagg ccgcggccga agggaaattc     2340
cacgtctatg cggtgtctca gtcgacgag gcgctggaac tcctcaccgg catcccggtg     2400
ggtcggcgtg acgaaaccgg cgtgttcccg gaaggttcgc tgaacaggaa ggtggaagaa     2460
cggctcaagg acttcgccgc ggtgctgcgc agcctgcaga gagcggcga agagacgggc     2520
ggggagaaac at                                                        2532
```

<210> SEQ ID NO 9
<211> LENGTH: 1911
<212> TYPE: DNA
<213> ORGANISM: Methylococcus capsulatus

<400> SEQUENCE: 9

```
atggccaaac actcccagca ttcctcccct ccccgcaagc tgttcgatac tttgaacgat       60
ctctggcagc gggcgaaaag cgaggccggc ctctcggccg aagtcccga gggcacccgc      120
cgccgcaaca acctgattct gtatctgttg ctggtgctgt ccaccctgta cctgctgaac      180
gggtatcaga ctctgcgcaa cgaggaaatt ccctacagcg aattcctgaa agcggtggcc      240
gaaggcagag tggaacaggc cgtggtcacc gagcagacca tttcgggcac cctcaagccc      300
```

-continued

```
gaagccgagg gtgaatcgac cggcccttc atcactgtgc cactgtggaa ccacgaactc      360
gccgcggaac tggaaaaaaa gggcgtgaaa tacacgtac gctatggcag taactggttc      420
agcagcctga tcttcaactg gatcgtcccc atcgttctgc tcaccctgtt ctggacctgg     480
atggcgcggc gcatgaccgg ggggagggga ttcctgagca tcggcaagaa gacccggatc     540
caggccgaca ccgccgccaa agtcacgttc ggcgacgtgg ccggcgccga cgaagccaag     600
caggagctgc gggaaaccat cgagttcctg cagaacccca cccgcatcca gagcctgggc    660
ggacgcatgc ccaagggcgt gctgctggtc ggcccacccg gcaccggcaa gactctcctg    720
gccccgcccg tcgccggcga agccggggtc ccgttcttca acatcagcgg ctcggagttc    780
atcgaactgt tcgtggggt cggtgccgca cgcgtccgcg acttgttcga acaggcccgc     840
cagaatgccc catgcatcat cttcatcgac gagctggacg ccatcggccg atcccgcggc    900
ggtccggtgg tgatgggtgg ccacgacgag cgcgagcaga ccctcaacca gctgctgacc    960
gagatggacg gcttcgaccc ctcggtcggc gtcgccgtga tggccgccac caaccgtccg   1020
gaaatcctgg acaaggctct gctccgctcc ggtcgcttcg accgccagat cgttgtggac   1080
aagccggggc tggaggaccg ggtttcgatc ctcaaactgc ataccgggaa gatgaaactg   1140
gcagcggatg tcgatctacg tgtggtcgcc cagcgcacac ccggcttcgt cggcgccgat   1200
ctggcaaacg ccgccaacga ggccgccatc atcgccgtac gcgcgaacaa ggccgccatc   1260
ggcatggcgg acttcgaggc tgccatcgac cgtatcctgg cgggtccgga agaagagc    1320 cggctgctca cgatgcaga gaagcaccgc gtggccgtcc acgaatccgg ccacgccctg    1380
gtcgccgaaa tcgtgccgac cggccaaccc gtgcacaagg tgtcgatcat tccccgcggc   1440
gccgcggccc tgggattcac cctgcagctt ccggtggaag agaaatttttt gtcgaccgag  1500 caggaactga aggatcagat cgccatcctc ctgggcggcc gcaccgcgga ggagctggtg   1560
ttcggcgaat cctccagcgg cgcccagaac gacctggaaa aggcttccga gatcgcccgc   1620
accatggttt gcagcctcgg aatgagcaag gtgctcggtc ccctcaccta cggccggcgt   1680
cagcagctcg cctacctcag cgtcgaaggc gccgaggaac gcaacttcag cgaggaaacg   1740
gcacggctga tcgacaacga ggttcggaaa ctgatcgagg aaggcttgca gcgcgtgcgc   1800
gaaatcctca cccaccaccg cgtcacactg gacaggctcg ccgccctgct ccgggaaaag   1860
gaagtcgtga gcggggaaga cgtcaaagcg gtgatccgcg aagcggcatc c            1911
```

<210> SEQ ID NO 10
<211> LENGTH: 1395
<212> TYPE: DNA
<213> ORGANISM: Methylococcus capsulatus

<400> SEQUENCE: 10

```
ttggaccctc ttgctatgcg gtttagaaag ataatcgata gaggtaattc catgcgcatg     60
aaatccatcg gcgcgctgtt gctactgacc gccagcggcc tgtccctctg cccccccggtg    120 tgggccgatt tgcccgccag cgtcaacggt ctgccactgc ccagcctcgc gcccgtcttg    180
aagaaggcca tgcccgcgt ggtcaacatc tcgacgaaga cccagatcga atcgccgag     240 aatcccctga tgcaagaccc cttcttccga catttcttcg gtattccgaa tcagccgcgg    300
cgccgtgaga gctccagcct cggctccggg gtgatcgtcg acgcccgccg aggctacatc    360
ctcaccaaca accatgtgat cgacaaggcg gacgagataa gcgtgacctt gagagacgga    420
cgccagttga gcgcaaaact ggtcggcgcc gatccggagt cggatttggc cgtcatcaag    480
gtcgaaccca agaatctgac ggaactgccc atcggtgatt cgagtcagct cgaagtcggc    540
```

-continued

```
gacttcgtgg tagccatcgg caatccctttt ggcctggggc agacagtgac ctccggcatc    600
gtcagtgccc tggggcgatc cggactcggc attgaggggt acgaggattt catccagacc    660
gacgcctcga tcaaccccgg caactcggga ggcgccttga tcaatctccg tggcgagctg    720
gtcggcgtga atacggccat catcgctccc accggcggaa acgtgggcat cggtttcgcc    780
atcccgtcca acatggccgc cagcatcatg acccaactgg tcgaaaaggg cgaaatccgc    840
cgcggccaga tcggcatcac catccaagac ctgacgccgg atctcgctca ggcctttggc    900
ctgaagcaga gccagggcgc ggtgatcacc ggcgtccaaa aggattcccc ggccgcatct    960
tcgggcctgg aagccggcga cgtcgtcgtc agcgtcaatg accgcccggt caaaaacagc   1020
gcggacgtcc gcaacaccat cggcctcctg cccataggcg aagaagtccg ggtcgaagtg   1080
atgcacaagg gggagagagt ggtacgcgag gtggtgatcc gcgcccccaa actggtccag   1140
gaagagggca ataaaatcca tcccagactg tccggtgtca tacttaagaa caacgaggag   1200
ggcggtgtcc aggtggaaaa aatccacacg agttcttacg ccttccaggc cggcctgcgc   1260
cccggcgacg tgatcgtgat ggcgaaccgc gaggaaatcg aaacgctcga tgacctgaag   1320
cgcgccacca agggccgctc ggagctgctc ctcagcgtcc agcggggcag cggctcgttc   1380
ttcttgatgc tgaag                                                    1395
```

<210> SEQ ID NO 11
<211> LENGTH: 830
<212> TYPE: DNA
<213> ORGANISM: Methylococcus capsulatus

<400> SEQUENCE: 11

```
atgcctaagt tcattcaaag aatcgccgcc gtctcggtag cggcggccct cggcctgagt     60
ggctgcgagt cgctgctgcc cgacttttac aaaaagccgg tttcaccgga gagcctgaag    120
atcgagaagg tgtcgaccga gcctccgccc gcgccgctgg cggaggccca gaccgacatg    180
ctcaagaagc cggagtacta tccgcggaag ggggccgtgg tcaatccgcc gtccgccggc    240
ggtggcggct acccgggttc cgccaccacg tcctccgctg gcggcggtgc gaccgggaaa    300
ggaggcggcc gcacctcgcc ccggaaagaa ggcaagtaca ccctcaattt cgacgacgcc    360
gacctgtcgg aagtcaccaa ggtcatcctc ggcgatacgc tgaaggtgaa ttacgtcctg    420
agtcccaagg tcaccggcaa ggtgagtctg cagaccaccc ggccgctgac cgaggacgag    480
atgatcccga cgctggagac cctgctgcgc atgaacgggg cggcgctgat ccggagggc    540
ggcatgtaca aaatcgaacc cgacgcccag gcggcgatca gcgcctccgg ccccggggtc    600
gggctgggaa tgatggagcc gggttaccag ttgcgggtca ttcctttgcg ttacatcagc    660
gccgcggaaa tgcagaaagt gctggagccc atcatgccgc ccaaggccgt gctgcggatg    720
gacgagaccc gcaatctggt catggtggcc ggtacggcgg aagagttggc ggcgtcatgg    780
aagcggtgca gattttcgac gtcgactaca tgcggggcag ggtaggtagg              830
```

<210> SEQ ID NO 12
<211> LENGTH: 429
<212> TYPE: DNA
<213> ORGANISM: Methylococcus capsulatus

<400> SEQUENCE: 12

```
atgaagcatc gacgtttcgt ccgtagtcgc agcggtttca ccctgatcga gctgctggtc     60
gtgctggcca tcatcgggct gctcgccgga ctgatcggtc cccaggtcat gaaacatctg    120
```

-continued

| | |
|---|---|
| ggcgagtcca agtccaagac cgcccgtctc cagatcgaag aactggcttc gtcgctggac | 180 |
| atgtacaagc tggacgtggg ccgttatccc accaccgatg aagggctgaa cgccctgatc | 240 |
| gaacagccca gcacggcgcg ggtctggaat ggcccttacc tgcgcaagaa gaaggttccg | 300 |
| ctggatccct ggaacaaccc gttccattac gtctcgccgg acagcacgg taagtacgac | 360 |
| ctctggtcgc tcggccagga caacgccgag ggcggcgaag gcgaggatgc cgatatcctc | 420 |
| ggctgggaa | 429 |

<210> SEQ ID NO 13
<211> LENGTH: 789
<212> TYPE: DNA
<213> ORGANISM: Methylococcus capsulatus

<400> SEQUENCE: 13

| | |
|---|---|
| gtgttgcggc gtttcctcga gatcctcgag ctaccccacg gtatcatcct gatcacggga | 60 |
| cccaccggca gcggcaaaag caccacgctg tataccgccc tgcacaagat caacacgcct | 120 |
| tcgcgcaaga tcatcacggt cgaggacccg gtggaatacc agctggaagg cgtcaaccag | 180 |
| atccaggtca gccccagat cggtctgaat ttcgcgagcg cgctgcgctc catcatgcgt | 240 |
| caggacccgg atgtgatcat gatcggtgag atgcgcgatc tggagacggc ccgtatcgcc | 300 |
| gtgcaatcgg cgctgaccgg ccacctggta ctgtccacgc tgcacaccaa tgacgccgcc | 360 |
| ggcggcgtga cccgtctttt ggacatgggg ctcgaggact atctcatcac ctcgaccgtg | 420 |
| aatggtattc tcggccagcg tctggtgcgg cggctgtgtc agagttgccg cgaaccacat | 480 |
| ccggcgctgg aggaggtcgc ggaagaaatg gggctgcggc ggttccagcg tgacggcgag | 540 |
| gtggtgctgt accggccggt cggctgcgaa caatgcggcg gcaccggttt cgtggacgg | 600 |
| ctcgcgatcc tcgagttcct ggtcatgtcc gacgaggtgc ggcggttggt gatgagtcac | 660 |
| gcccaggcgc ggcagatcga ggaggtcgcc ctacgcgaag gcatgcatac catgtatgac | 720 |
| gatggtgtcc gcaaggcttt gatggggctg accaccgtcg aagaggtcct gcgcgtcacc | 780 |
| tcggattcc | 789 |

<210> SEQ ID NO 14
<211> LENGTH: 1437
<212> TYPE: DNA
<213> ORGANISM: Methylococcus capsulatus

<400> SEQUENCE: 14

| | |
|---|---|
| atgaataagc ccgcgtttgc cgctttattg ctgtcacttt tggcgccagc cgcttccgcc | 60 |
| gtcgatctgc tcggcgtatt cgatctcgca ctgcaatacg atccccgtct gcatgcggcg | 120 |
| caggcccagc gcgacgcggc gctcgagaac aagccgcagg ccgtggcccg gctgctgccg | 180 |
| acggtgtccg ccaccaccgg actgacccga cagatggtcc agaccggtga ctcgcccatc | 240 |
| ctggtgttca cgccaaaaa gaacgtcggt ttctggctgg cgaccggcat cgtgcagctg | 300 |
| gtgcagccta tctaccagca cgacctgtgg gtgcggctgg cccaggccga caatgcggtg | 360 |
| gccgaagccg aagcccttcta cgcggcgaaa ctgcagagcg tgatgctacg ggtgacccag | 420 |
| acctatttcg aggtcctgta caaggaagcg tcgctggact tcgccagggc cgaactggag | 480 |
| tcgatcaatc gggagctgga gcaggccaat gcccgcttcg aggtcggcct gtcgcggtg | 540 |
| accgacgtga acgaggcgca ggcggcggcg gacagggcg gggcgggcgt catcatcgcc | 600 |
| gaaaacgagc tgaacaacgc ccgggagcat ctgcgccaga tcgtgggtga cgatccgggc | 660 |
| gagctggaac cgctgaagct cgaagtgccg ttggaagatc caatgccgga cgacatcgag | 720 |

```
cgctggaacg acaccgccca gcagagtgcg ctgaccatca tcgccgcgac caaccgggca    780
gaccgggcca aacaggaaat cgaggtgcag ttcgccgggc actatccttc gatcaacctg    840
atcgccgatg cccagttcta tgacaatgac cggccgcccc gccccaaccg ctaccagcag    900
caggacgtgg gcatgcagat caacgtgccg ctgttcgcgg gcggcggggt caattcccgg    960
gtccggcagg cgcgcttcgg cttcgaagcc gccatccagc agctggacca ggagcgccgc   1020
gcggtacgca ccagggtgaa gaatgcctat cgggccatcc gctccgccat cggccaggcc   1080
aaggccttca aaaccgcgat caaatcgtcg gaaagcgcac tggaggccgc catcgccggc   1140
atggaggtcg gcacccgcac catgacggac gtgctgttcg tacagcgcca gtattaccag   1200
aacaaacgcg acttcgccct ggccctgcgc gactacatcg tcaacagcgt cgcgctgaag   1260
gaagccgcca gcgtcatgca gcgcgaggac ctggaccgga tcaacggctg gctacaggcc   1320
ccgcccgcag cgccggcgaa ggacgggacc ggagccgcgc ccatgcaacc gggatccggg   1380
ccggtccgca aggccggccg aggcgccccg gcgccaagcg ctccgaatct tcaccgc      1437
```

SYSTEMS FOR EXPRESSION OF HETEROLOGOUS PROTEINS IN *M. CAPSULATUS*

FIELD OF THE INVENTION

The present invention relates to the expression of heterologous proteins in the bacteria *M. capsulatus*. More specifically, the present invention relates to the exportation and display of polypeptides and proteins on the surface of said bacteria.

BACKGROUND OF THE INVENTION

The expression of polypeptides on the surface of bacteria and bacteriophage has been pursued for several years, in part because of interest in recombinant antibody production. Many other potential applications exist, including the production of genetically-engineered whole cell adsorbents, construction of "peptide libraries", cell bound enzymes, and use as live vaccines or immunogens to generate antibodies.

In bacteria, one approach to obtaining surface expressed foreign proteins has been the use of native membrane proteins as a carrier for a foreign protein. In general, most attempts to develop methods of anchoring proteins on a bacterial surface have focused on fusion of the desired recombinant polypeptide to a native protein that is normally exposed on the cell's exterior with the hope that the resulting hybrid will also be localized on the surface.

BRIEF SUMMARY OF THE INVENTION

The present invention also provides an expression system where a heterologous polypeptide (termed "desired" protein) is expressed in the bacteria *Methylococcus capsulatus*. The heterologous protein is preferably linked to one of the outer membrane proteins in *M. capsulatus*. These outer membrane proteins have been identified based on sequence homology studies, and the novel sequences of these proteins are claimed.

The identified sequences given as SEQ ID NO 1 to SEQ ID NO 4 are nucleotides which codes for the proteins MopC, MopD, MopE and MopF, respectively. The present invention further claims the sequence given in SEQ ID NO 5, which is identified as D15, and the sequences given as SEQ ID NO 6 to SEQ ID NO 14 as these sequences are identified as helper proteins.

The present invention thus relates to a nucleotide molecule wherein the molecule has a sequence which codes for a nucleotide sequence selected from the group comprising SEQ ID NOS 1–14. Preferable the nucleotide molecules codes for a surface exposed protein.

The nucleotide molecule is further linked in frame to the nucleotide molecule which codes for a desired peptide or protein. This protein may be a drug.

The present invention also relates to a recombinant vector comprising a first nucleotide sequence selected from the group comprising SEQ ID NO 1 to SEQ ID NO 14.

The present invention also relates to a recombinant vector, wherein the nucleotide sequence further comprises a second nucleotide sequence.

Further, the invention relates to a bacterial host cell transformed with the recombinant vector. Preferably, the bacterial cell is *M. capsulatus*.

Further, the invention relates to a method for producing a desired protein in a bacterial host cell, said method comprising transforming a bacterial host cell with a recombinant vector comprising a first nucleotide sequence from the group comprising SEQ ID NO 1 to SEQ ID NO 14, and said vector comprising a further nucleotide sequence encoding said protein, said further nucleotide sequence being operably linked in frame to said first nucleotide sequence, and culturing said transformed host cell in a suitable medium under conditions allowing expression of said protein.

A preferred embodiment of the invention uses the method to produce a medicament which can be administered orally.

The invention also relates to proteins capable of being exposed on the surface of a methonotrophic bacterium, wherein the protein is encoded by a nucleotide sequence selected from the group comprising SEQ ID NO 1 to SEQ ID NO 14, and fusion proteins containing a protein or peptide sequence encoded by a nucleotide sequence selected from the group comprising SEQ ID NO 1 to SEQ ID NO 14, and a further desired protein or peptide.

The broadest concept claimed in the present invention is a system for the expression of heterologous proteins in the *M. capsulatus*. We have shown that it is possible to express a protein portion of a virus in the *M. capsulatus*, and the present invention thus for the first time describes an expression system in said bacterium.

A further object of the present invention is to provide an expression system where the desired heterologous protein is presented on the surface of the bacterial cells. We have thus identified several membrane proteins which can be used as transporter proteins for the desired heterologous passenger proteins, in order to translocate the desired protein to the membrane. Preferable the desired proteins are located on the outer side of the membrane.

The fusion protein according to the invention is preferable expressed from a chimeric DNA having a DNA segment encoding a leader amino acid sequence capable of mediating secretion of the fusion protein, a DNA segment encoding for subunits of the surface protein, and a DNA segment encoding the desired target protein. The DNA segments are positioned such that expression of the fusion protein results in display of the target protein on the surface of the cells. The fusion proteins are preferably anchored to the cell surface of the bacteria forming what is referred to as a "display bacteria."

The present invention thus provides for a system for the expression of heterologous proteins, where the heterologous proteins are expressed on the surface of the bacterial cells.

The chimeric DNA may be integrated into the bacterial cell chromosome or be carried by a vector. In certain preferred embodiments, expression of the fusion protein may be regulated by an inducible promoter. Bacteria displaying a particular protein may be selected, for example, using antibody affinity. The fusion protein can be detached from selected cells. If desired, the target protein may be separated from the surface protein and further purified.

Target proteins useful in the present invention include peptides, proteins, e.g., hormones, enzymes, inhibitors, and receptors, antigens, antibodies including antibody fragments and single-chain antibodies.

The present invention thus provides a system for the expression of heterologous proteins in the membrane fraction, and preferable on the cell surface of the *M. capsulatus*.

The bacterium *M. capsulatus* is able to utilise methane as a single carbon and energy source. Bacteria capable of oxidising methane is collectively referred to as methanotrophs. They belong to different families and groups of the eubacteria but have in common the possession of the unusual enzyme methane monooxygenase, which catalyses the oxidation of methane to methanol.

The bacterium has an obligate requirement for methane or methanol and an optimum growth temperature of 45° C. Methane is oxidized via methanol to formaldehyde which is either assimilated into cellular biomass or dissimilated to carbon dioxide to release cellular energy.

*M. capsulatus* has a gram-negative cell envelope. Much of the intracellular space is occupied by an extensive intracytoplasmic membrane system. The genome of *M. capsulatus* (Bath) has a molecular weight of $2.8 \times 10^9$ Da and a G+C content of 62.5%.

Commercial interests involving *M. capsulatus* and other methanotrophs could roughly be divided into two categories: Those taking advantage of the inexpensive growth requirements of the bacteria and those taking advantage of unique catalytic activities possessed by the bacteria.

The development of high-cell density fermentation technology for *M. capsulatus* has created the possibility of producing large quantities of specialised compounds like amino acids, cofactors, vitamins, metabolic end products, and various high value proteins, at reasonable costs.

The present invention thus provides a system for the manufacturing of such product.

Other uses for the protein display methods of the present invention include, for example, epitope mapping, screening of antibody libraries and live bacterial vaccines.

In a co-pending application, the inventors of the invention provide data for several of the genes in the genome of the *Methylococcus capsulatus*. Some of these genes are sharing significant homology with genes encoding surface proteins in other bacteria, and the proteins encoded by these genes could be used in an expression system to transport heterologous proteins to the surface of methanotrophic bacteria. These findings are exemplified by the establishing of a fusion protein of MopE from *M. capsulatus* and the VP2 proetin of the infectious pancreatic necrosis (IPN) virus, as detailed in the experimental section.

The invention is especially suited for production of vaccines that can be administered orally for use in animals, fish and humans. The technique can also potentially be used for display of vaccines, especially for oral administration.

The invention relates to the use of the genes and the proteins encoded by them, as given in the accompanying sequences list, fragments thereof, or functionally equivalent substantially homologous genes, for construction of fusion proteins carrying foreign peptide sequences for display in the *M. capsulatus*, and preferable on the surface of said bacterium.

"Substantially homologous" as used herein defines sequences displaying at least 80% sequence identity and also functionally equivalent allelic variants and related genes modified by single or multiple base substitutions or addition and/or deletion.

Surface proteins in accordance with the present invention are the outer membrane proteins MopC (SEQ ID NO 1), Mop D (SEQ ID NO 2), MopE (SEQ ID NO 3) and MopF (SEQ ID NO 4).

Further, one of the genes (SEQ ID NO 5) encodes a homologue of a surface protein-antigen (sometimes termed D15) identified in a variety of Gram-negative bacteria.

Further, the present inventors have identified several proteins involved in the presentation of the above mentioned proteins on the surface. These proteins are in this context termed "helper proteins", and are encoded by the sequences SEQ ID NO 6 to 14.

BRIEF DESCRIPTION OF THE DRAWINGS

The results obtained are given in the FIGS. 1–5, wherein.

DETAILED DESCRIPTION OF PREFERRED EMBODIMENTS OF THE INVENTION

Figure 1:
FIG. 1 shows the two fusion constructs cloned in *Methylococcus capsulatus*.

The *M. capsulatus* surface-antigen homologue (D15) is a large protein with a molecular weight about 80 kD sharing about 50% sequence identity with the corresponding protein from *Pseudomonas aeruginosa*. The similarity with other Gram-negative bacteria is in the range 39 to about 20% identity. These bacteria include many important human pathogens, like *Vibrio cholerae* (39% identity), *Shigella flexneri* (38% identity), *Neisseria meningitidis* (36% identity), *Haemophilus influenzae* (32%), *Campylobacter jejuni* (23%), *Borrelia burgdorferi* (21%), and animal pathogens such as *Pasteurella multocida* (34%) and *Brucella abortus* (28%). When used for immunization of experimental animals, the D15 protein from *H. influenzae* and *P. multocida* has been shown to trigger an immune response that protects the immunized animals against infection by the respective bacteria.

Thus, the D15 antigen as a protein class has proven to be an immunogenic protein, and use of the D15 antigen as a vaccine against a variety of diseases caused by Gram negative bacteria is a promising idea. Many other pathogens within the genera *Vibrio* and *Shigella*, as well as related genera, probably also possesses a D15 antigen, but have not yet been characterized by sequencing of their genes. Several important fish pathogens which belong to genus *Vibrio* and the related genus *Aeromonas*, probably also contain this antigen. There is a great demand for efficient and inexpensive vaccines for protection against infections caused by all the bacteria mentioned above, and many more could be listed.

*M. capsulatus* is a bacterium licensed for use in animal and fish feed. It has no virulent or pathogenic properties, and contains very low amounts of endotoxin (LPS). It is thus well suited as a carrier organism for recombinant oral vaccines, with a potential also for use in humans. Vaccines could be constructed by insertion of fragments of D15 genes from pathogens into the *M. capsulatus* D15 gene in order to display a fusion-protein containing parts of the two D15 antigens on the surface of *M. capsulatus*. The part of the D15 protein originating from the pathogen should trigger an immune response to the respective pathogenic bacterium. If replacement of *M. capsulatus*-specific D15 sequences with corresponding sequences from the pathogens is well tolerated by the host, larger regions of D15 could be replaced, and if possible, the entire D15 protein could be replaced by the corresponding protein from a pathogen.

Due to the sequence conservation of D15 among distantly related bacteria, exchange of parts of the gene (or the entire gene) without seriously affecting the survival and growth of *M. capsulatus* is plausible. The specific function of the D15 antigen on the surface of the bacteria is not known, but it possibly plays a structural role and is most probably not involved in any important biochemical processes.

Successful display of the target protein on the cell surface can be detected using a number of methods, for example, if the target peptide can be specifically labeled by a procedure that does not operate through the membrane, its cell surface display can be readily demonstrated.

If the target polypeptide displays enzymatic activity, one may use such activity to demonstrate cell surface display. Antibodies against the target protein may also be used.

The chimeric DNA may be integrated into the host cell chromosome or be carried within a vector. Methods of integrating DNA into a host cell chromosome are well known in the art. The chimeric DNA may also be carried within a recombinant vector, e.g., a plasmid.

Plasmids useful as the vector backbone include plasmids containing replicon and control sequences which are derived from species compatible with the host cell. The vector may also contain an inducible promoter and marker gene, e.g., antibiotic resistance.

Introduction of the chimeric DNA to the host cell may be effected by any method known to those skilled in the art. For example, if a recombinant vector carries the DNA, the vector can be introduced, for example, by transformation, electroporation, or phage transfection.

The detection techniques noted above can be used initially to verify that the method of the present invention is working, i.e., that the fusion surface protein has been expressed and transported to the bacterial cell surface and is orientated so that the target protein is accessible i.e., displayed.

Cells that display the target may be separated from those that do not, using, for example, affinity separation techniques. Such techniques include affinity column chromatography, batch elution from affinity matrix material and fluorescent-activated cell sorting.

MopE is a major outer membrane protein of *M. capsulatus*. It contains surface-exposed regions but its exact folding and association with the cell surface is not known. Under copper limitations, the C-terminal part of the protein is secreted into the growth medium, but considerable amounts of the full-length protein remains associated with the cell surface. By using this protein as an anchor it is possible to mediate translocation of passenger proteins to the cell surface or to the extracellular environment. Other outer membrane proteins according to the invention are MopC, MopD and MopF. These outer membrane proteins share structure similarities and it is thus anticipated that also these proteins can be used for the expression of heterologous proteins in *M. capsulatus*.

In order to establish the expression system according to the invention, and to illustrate the concept of the invention, fusion proteins composed of MopE and the VP2 protein of the infectious pancreatic necrosis (IPN) virus were constructed. The proteins were expressed in *M. capsulatus* (Bath) and their location within the cell was investigated.

Bacterial Strains and Growth Conditions

*M. capsulatus* (Bath) was obtained from the National Collections of Industrial and Marine Bacteria (NCIMB 1132). *E. coli* DH5 was used for routine cloning purposes and *E. coli* S17-1 was used as a donor strain in the conjugation experiments. Both strains were grown in Luria-Bertani (LB) medium supplemented with the appropriate antibiotic. *M. capsulatus* was grown with methane as a carbon source in nitrate mineral salts (NMS) medium (Whittenbury et al. 1970). Cells grown in medium supplemented with 1 mg/l $CuSO_4 \cdot 5H_2O$ are referred to as "high copper cells". Cells referred to as "low copper cells" were grown in NMS with no copper added and containing the modifications of Stolyar et al. (1999).

Recombinant DNA Techniques

Four different DNA fragments were amplified by PCR. These encoded the immediate upstream region of the smmo operon, the N-terminal region of MopE, the F2 region of the VP2 protein, and the C-terminal, secreted region of MopE. The primers used for the amplifications are listed in Table I.

TABLE I

| PCR amplification product[a] | Nucleotide sequences of primers used to amplify DNA fragments | | |
|---|---|---|---|
| | Primer sequences[b] | | |
| smmo upstream region (1500) | 5'-CGGATCGTTGAGCTCTTTTCCCATC-3' (SacI) | (SEQ ID. No 15) | |
| | 5'-GCTAAGTGCCATATGTTGTTTCCTC-3' (NdeI) | (SEQ ID. No 16) | |
| MopE N-terminal region (722) | Sp6 primer (Promega) | (SEQ ID. No 17) | |
| | 5'-GCGTGTCCAGGatCcCGGAGTTCGCTG-3' (BamHI) | (SEQ ID. No 18) | |
| F2 region of VP2 protein (581) | 5'-CTAACAACGAACCagatctACAAAGTCAACAAC-3' (BgIII) | (SEQ ID. No 19) | |
| | 5'-GAGAAGGAGACGGggatccGACCCATTGTG-3' (BamHI) | (SEQ ID. No 20) | |
| MopE C-terminal region and downstream | 5'-CAGCGAACTCCGgGatCCTGGACAC-3' (BamHI) | (SEQ ID. No 21) | |
| termination signal | 5'-GCTGGAAAAAGCatgCGCCCAACTC-3' (SphI) | (SEQ ID. No 22) | |

[a]Length of PCR product in bp are shown in parentheses
[b]Restriction endonuclease sites contained in the primers are shown in parentheses and their position within the primers are underlined. Mismatched nucleotides are in lowercase letters.

DNA fragments encoding the N- and C-terminal domain of MopE were amplified by PCR from the plasmid pAFpg10 (Fjellbirkeland et al. 2001). The F2 region of the VP2 protein was amplified from a plasmid containing the entire genome of VP2 (kindly provided by E. Bjering, NorBio). The 1500 bp immediate upstream region of the smmo operon was amplified from chromosomal DNA. The PCR products were cleaved with appropriate restriction enzymes and inserted into plasmid pJB3 Kml (Blatny et al. 1997). DNA was sequenced using the ABI PRISM BigDye Terminator Cycle Sequencing Ready Reaction Kit and the DNA sequencer at the University of Bergen Core Facility.

Conjugation

Conjugation between *E. coli* S17-1 (donor strain) and *M. capsulatus* was carried out essential as described by Lloyd et al. (1999). 10 ml of an over-night culture of *E. coli* S17-1 containing the recombinant mopE product was washed by centrifugation (7000 rpm for 5 min) and resuspended in 10 ml NMS. The *E. coli* suspension was mixed with 50 ml *M. capsulatus* (1.8 $10^8$ cells/ml; $A_{600}$=0.22) and filtered down on a 0.2 μ nitrocellulose filter. The filter was incubated on NMS-agar plates under an atmosphere of methane:air:$CO_2$ (48:50:2) at 42° C. for 14 h. The conjugation was terminated by vortexing the filter in 10 ml NMS. To select for recombinant *M. capsulatus*, 200 Ïl of the cell suspension from point 4 was plated on NMS-agar plate with 30 Ïg/ml kanamycin as selective agent. The plate was incubated under an atmosphere of methane:air:$CO_2$ (48:50:2) until visible growth was obtained. *M. capsulatus* grown with 30 Ïg/ml kanamycin was shown to contain plasmid with recombinant mopE.

SDS-PAGE and Western Blotting

SDS-PAGE and Western blotting were performed as described previously (Fjellbirkeland et al. 2001). Anti-MopE antiserum was produced as described (Fjellbirkeland et al. 1997). Anti-VP2 antiserum and F2 monoclonal antibodies were provided by E. Bjering, NorBio.

Differential Fractionation of *M. capsulatus*

Outer membranes were isolated from *M. capsulatus* as described previously (Fjellbirkeland et al. 1997).

The 5'-end of the mopE gene was ligated to DNA encoding the F2 region of the VP2 protein of the IPN virus. The F2 region is a conserved neutralizing epitope of IPN virus and is thus regarded as an important component of a potential subunit vaccine against IPN in fish (Frost et al. 1995). The mopE 5'-end encoded the part of MopE that is not secreted into the growth medium. The secreted protein starts with a glycine and cleavage occurs between $Ala_{204}$, and $Gly_{205}$ of the mature protein (Fjellbirkeland et al. 2001). In order to prevent cleavage and secretion of the IPN peptide, the two amino acids in the cleavage region were changed to glycine and isoleucine, respectively. Since the C-terminal part of MopE is secreted, it seems likely that the N-terminal region of the protein is responsible for anchoring MopE to the cell wall. To investigate whether the N-terminal fragment was sufficient for outer membrane translocation of the heterologous passenger peptide, a deletion protein composed of the N-terminal non-secreted domain of MopE and the virus epitope was constructed (Constructa, FIG. 1). In Construct b (FIG. 1) the viral peptide was inserted between the N-terminal and C-terminal domain of MopE. This allowed investigations of the importance of the C-terminal part of MopE for membrane translocation.

A DNA sequence corresponding to the 1500 bp immediate upstream region of the smmo operon (Stainthorpe et al. 1990) was inserted in front of the fusion genes. Transcription of sMMO is regulated by copper (Nielsen et al. 1996; 1997). Thus, by including this promoter element it should be possible to repress/induce expression of the fusion protein by manipulating the copper level in the growth medium.

Figure 2:
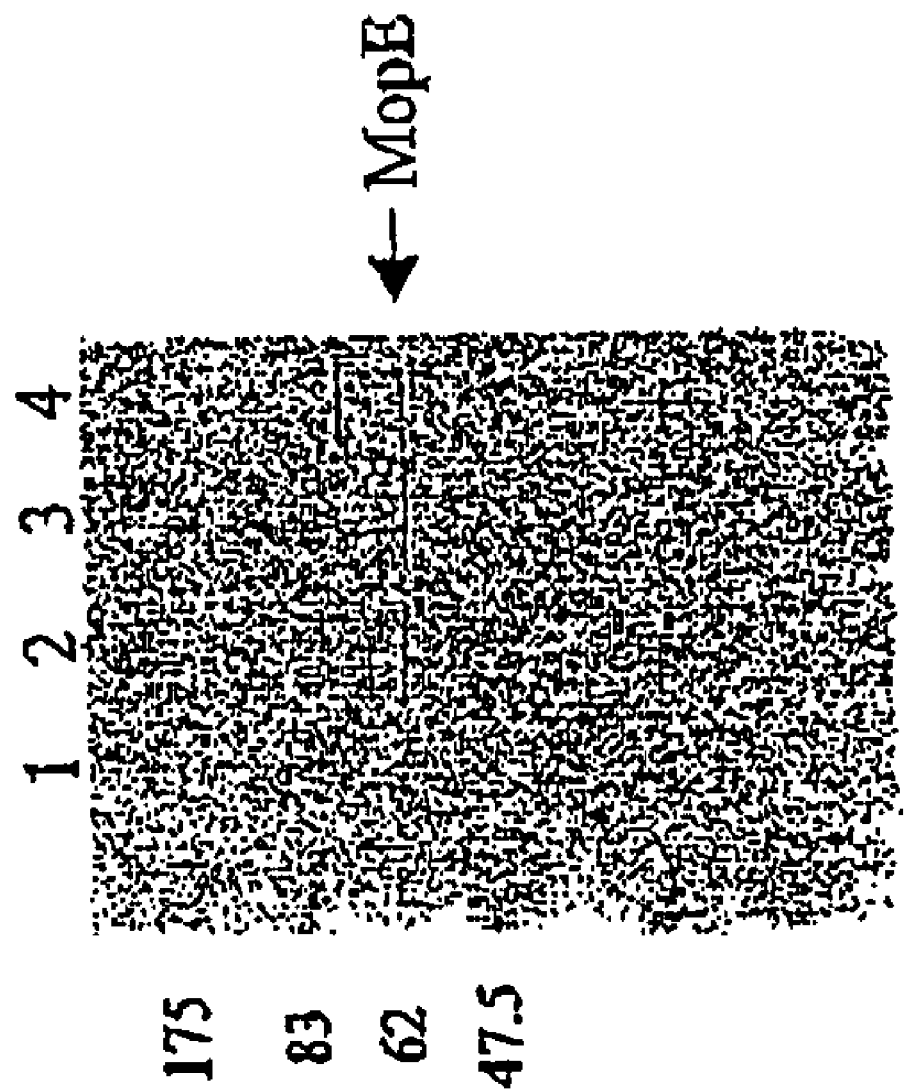
FIG. 2 presents the Western blot treated with anti-MopE antiserum of *M. capsulatus* grown in low-copper medium. Cells contained no plasmid (lane 1), plasmid pJB3KM1 (lane 2), Construct a (lane 3), and Construct b (lane 4).

The constructs were ligated into a broad-host-range plasmid and cloned in *E. coli* S-17. The plasmids were subsequently transferred to *M. capsulatus* by conjugation. Sequencing verified that the conjugated plasmids contained the correct inserts and that PCR had not resulted in mutations of the fusion genes. The recombinant cells were grown in a low-copper medium that enhances sMMO expression (Stolyar et al. 1999) and analyzed by Western blotting. Cells containing no plasmid and cells containing the plasmid only were used as negative controls. Anti-MopE antiserum recognized a band corresponding to MopE in all cells (FIG. 2). In cells containing Construct b, three additional bands were recognized (FIG. 2, lane 4). These had approximately molecular weights of 40, 60 and 80 kDa. The calculated molecular weight of the fusion protein of Construct b is 75 kDa. MopE migrates slightly above its calculated molecular weight in SDS-PAGE (Fjellbirkeland et al. 2001) and thus the 80 kDa band most likely represents the entire fusion protein. The 40 kDa and 60 kDa band could represent truncated versions of the fusion protein but their composition will have to be studied more closely. In cells containing Construct a no fusion protein could be detected indicating that the C-terminal part of MopE is important for stabilization of the protein.

Figure 3:
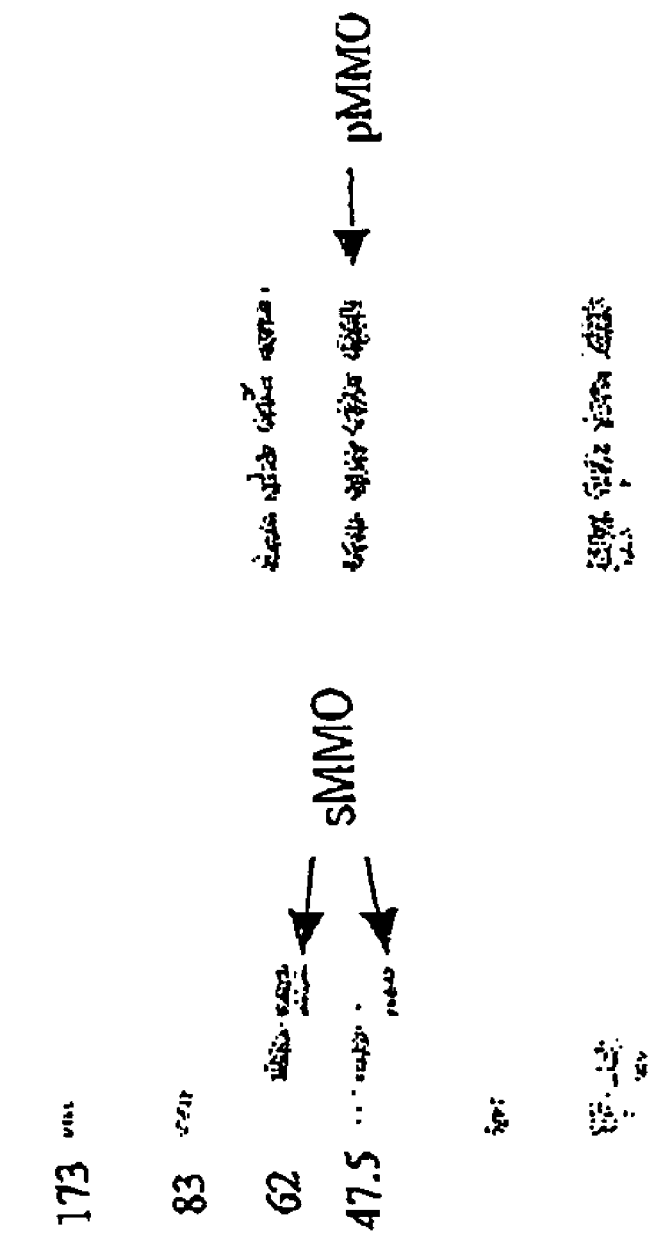
FIG. 3 is the SDS-PAGE of *M. capsulatus* grown in high and low copper media. High copper (lane 1) and low copper cells (lane 2) grown in fermentor (kindly provided by CJ Murrell, University of Warwick). The cells run in lanes 3, 4, 5 and 6 are identical to those of lanes 1, 2, 3, and 4 in FIG. 2, respectively.

The immunoblots were also treated with polyclonal and monoclonal VP2 antiserum. These did not recognize any of the fusion proteins. This could be due to the low levels of fusion protein produced by the cells. The recombinant cells contain several copies of the plasmid and provided the promoter that drives the expression of the fusion protein is not repressed, a relatively high level of recombinant protein should be produced. The low level may thus be a result of an inefficient promoter. To investigate this, the level of sMMO was analyzed by SDS-PAGE. The gel demonstrated that pMMO rather than the sMMO was the dominant methane monooxygenase produced by the cells (FIG. 3) indicating that the smmo promoter was repressed.

Figure 4:
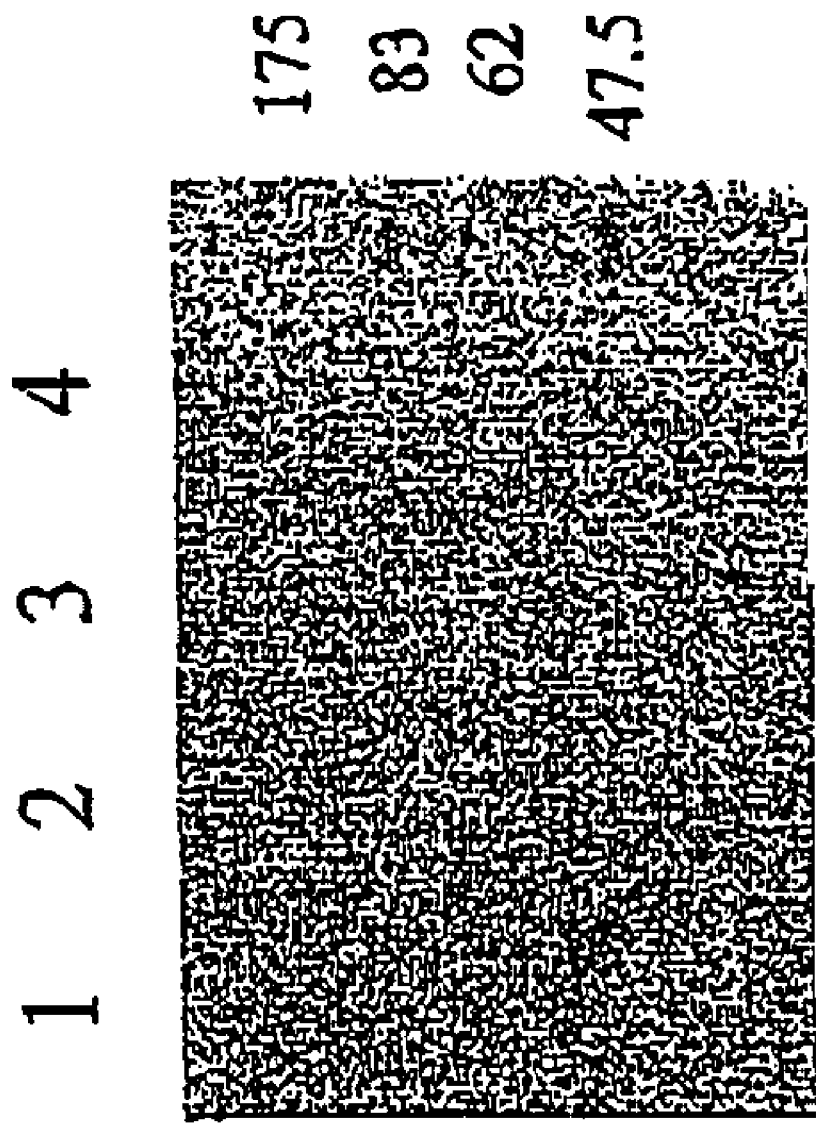
FIG. 4 shows the Western blot treated with anti-MopE antiserum of *M. capsulatus* grown in high copper medium. Cells contained Construct b (lane 1), Construct a (lane 2), plasmid pJB3KM1 (lane 3), and no plasmid (lane 4).

The level of fusion protein in cells grown in high copper media was also analyzed. On Western blot treated with anti-MopE antiserum, low levels of fusion protein was detected (FIG. 4). This further strengthened the assumption that production of fusion protein by the low copper cells was due to leakage from a repressed promoter. Like sMMO production, MopE production is regulated by the copper level in the medium (unpublished results), and MopE could not be detected in the high copper cells. However, the 40 and 80 kDa polypeptides could be detected in cells containing Construct b, and this clearly demonstrates that these polypeptides are produced from a promoter different from the MopE promoter.

Figure 5:
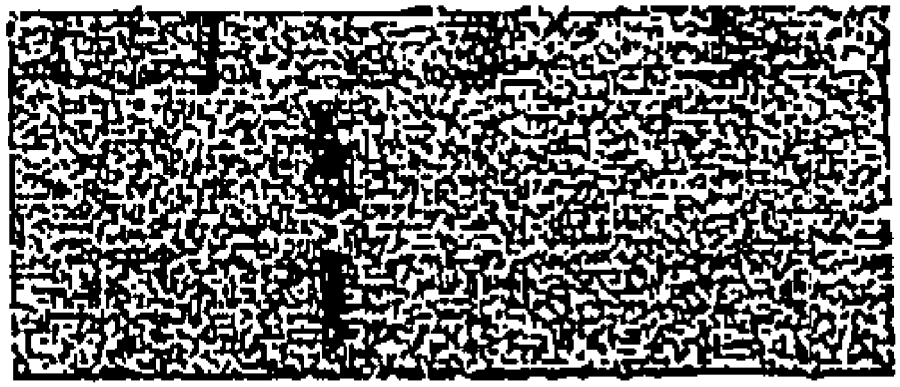
FIG. 5 shows the Western blot treated with anti-MopE Antiserum of outer membranes isolated from *M. capsulatus* grown in low copper medium Cells. contained plasmid pJB3KM1 (lane 1) and Construct b (lane 2).

The low copper cells containing Construct b were fractionated in order to determine the cellular location of the recombinant polypeptides. The 40 kDa band was detected in the soluble fraction containing cytoplasmic and periplasmic proteins (not shown). A faint 80 kDa band was detected in the outer membrane as well as a high molecular band which could represent a dimer of the fusion protein (FIG. 5). However, due to the low level of fusion protein and the enrichment of MopE in the outer membranes, it is difficult to discriminate between fusion proteins and MopE aggregates in the gel.

A fusion protein of which a viral epitope has been inserted between the N-terminal non-secreted and C-terminal secreted domains of MopE has been expressed in *M. capsulatus*. The smmo promoter is repressed in low-copper media but the growth condition used in this study did not seem to derepress the promoter completely. It is possible that growth of the recombinant cells in a fermentor rather than flasks will result in more efficient expression of the fusion protein since fermentor grown cells switch more efficiently between sMMO and pMMO production than cells grown in flasks (Stanley et al. 1983).

A DNA construct composed of only the N-terminal non-secreted part of MopE and the viral epitope did not produce any detectable fusion protein. This indicates that the C-terminal part of MopE is required in order to obtain a stable protein product. It should be noted, however, that the fusion gene of Construct b was followed by the RNA polymerase termination signal of MopE. The fusion gene of Construct a was followed by plasmid sequence and this may have resulted in unstable, not properly terminated RNA. It is thus possible that propagation of Construct a in an expression vector will result in production of a stable fusion protein.

The 80 kDa fusion protein appeared to be transported to the outer membrane of *M. capsulatus*. However, due to the enrichment of MopE in the outer membrane and the low levels of fusion protein, it was difficult to determine whether the observed high molecular bands represent the fusion protein or aggregates of MopE.

It has been demonstrated that it is possible to express heterologous peptides in *M. capsulatus* by using the native protein MopE as a fusion partner. The results indicate that the fusion protein is transported to the outer membrane but more research will be needed in order to be able to determine more specific which parts of MopE that are required for surface display/secretion.

REFERENCES

Blatny J M, Brautaset T, Winther-Larsen H C, Haugan K, Valla S. (1997). Construction and use of a versatile set of broad-host-range cloning and expression vectors based on the RK2 replicon. Appl Environ Microbiol. 63: 370–379

Fjellbirkeland A, Kruger P G, Bemanian V, Hogh B T, Murrell J C, Jensen H B. (2001) The C-terminal part of the surface-associated protein MopE of the methanotroph *Methylococcus capsulatus* (Bath) is secreted into the growth medium. Arch Microbiol. 176: 197–203.

Frost P, Havarstein L S, Lygren B, Stahl S, Endresen C, Christie K E. (1995) Mapping of neutralization epitopes on infectious pancreatic necrosis viruses. J Gen Virol. 76: 1165–72.

Lloyd J S, De Marco P, Dalton H, Murrell J C. (1999) Heterologous expression of soluble methane monooxygenase genes in methanotrophs containing only particulate methane monooxygenase. Arch Microbiol 171: 364–370

Nielsen A K, Gerdes K, Degn H, Murrell J C. (1996) Regulation of bacterial methane oxidation: transcription of the soluble methane mono-oxygenase operon of *Methylococcus capsulatus* (Bath) is repressed by copper ions. Microbiology. 142: 1289–1296.

Nielsen A K, Gerdes K, Murrell J C. (1997) Copper-dependent reciprocal transcriptional regulation of methane monooxygenase genes in *Methylococcus capsulatus* and *Methylosinus trichosporium*. Mol Microbiol. 25: 399–409.

Stainthorpe A C, Lees V, Salmond G P C, Dalton H, Murrell J C. (1990). The methane monooxygenase gene cluster of *Methylococcus capsulatus* (Bath). Gene 91: 27–34

Stanley S H, Prior S D, Leak D J, Dalton H. (1983) Copper stress underlies the fundamental change in intracellular location of methane mono-oxygenase in methane-oxidizing organisms: studies in batch and continuous cultures. 7: 487–492

Stolyar S, Costello A M, Peeples T L, Lidstrom M E. (1999) Role of multiple genecopies in particulate methane monooxygenase activity in the methane-oxidizing bacterium *Methylococcus capsulatus* Bath. Microbiology 145: 1235–1244

Whittenbury R, Phillips K C & Wilkinson J F (1970) Enrichment, isolation and some properties of methane-utilizing bacteria. J. Gen. Microbiol. 61: 205–218

The invention claimed is:

1. An isolated nucleotide molecule wherein the molecule has a sequence comprising the sequence of SEQ ID NO 3.

2. The nucleotide molecule according to claim 1, wherein the nucleotide molecule codes for a surface exposed protein.

3. The nucleotide molecule according to claim 1, wherein the nucleotide molecule further comprises a nucleotide sequence that encodes for a desired peptide or protein.

4. The nucleotide molecule according to clam 3, wherein said peptide or protein is a drug.

5. The nucleotide molecule according to claim 3, wherein said peptide or protein is an antigen or an antibody.

6. The nucleotide molecule according to claim 1, wherein the nucleotide further comprises a gene that encodes for a selection marker.

7. The nucleotide molecule according to claim 6, wherein the selection marker is an antibiotic selection marker.

8. The nucleotide molecule according to claim 7, wherein said antibiotic selection marker is kanamycin.

9. A recombinant vector comprising a first nucleotide sequence comprising the sequence of SEQ ID NO 3.

10. The recombinant vector according to claim 9, wherein the nucleotide sequence further comprises a second nucleotide sequence.

11. The recombinant vector according to claim 10, wherein said second nucleotide sequence has multiple cloning sites, and said multiple cloning sites are positioned such that insertion of a third nucleotide sequence into any one of said cloning sites operably links said third nucleotide sequence to said first nucleotide sequence.

12. The recombinant vector according to claim 11, wherein said third nucleotide sequence codes for a desired protein or peptide.

13. The recombinant vector according to claim 12, wherein said protein or peptide is a drug.

14. The recombinant vector according to claim 13, wherein said protein or peptide is an antigen or an antibody.

15. The recombinant vector according to claim 9, wherein said nucleotide sequence further comprises a gene that codes for a selection marker.

16. The recombinant vector according to claim 15, wherein said selection marker is an antibiotic selection marker.

17. The recombinant vector according to claim 16, wherein said antibiotic selection marker is kanamycin.

18. The recombinant vector according to claim 9, wherein said nucleic acid further comprises a replication origin that functions in the host *M. capsulatus*.

19. The recombinant vector according to claim 18, wherein said replication origin is smmo.

20. The recombinant vector according to claim 18, wherein said replication origin is pmmo.

21. The recombinant vector according to claim 12, wherein the desired protein is expressed in the membrane fraction of *M. capsulatus.*

22. The recombinant vector according to claim 21, wherein the desired protein is expressed on the surface of the outer membrane of *M. capsulatus.*

23. The recombinant vector according to claim 12, wherein the nucleotide coding for the desired protein contains a region which codes for a peptide stretch which functions as a substrate for a hydrolyzing enzyme capable of cleaving the desired protein from the remaining membrane anchored proteins, such that the desired protein is excreted to the culture medium.

24. The recombinant vector according to claim 9, wherein the recombinant vector is a plasmid.

25. The recombinant vector according to claim 24, wherein the plasmid is pAFpg10.

26. A bacterial host cell transformed with the recombinant vector according to any one of claims 9–25.

27. The bacterial host cell according to claim 26, wherein the bacterial cell is *M. capsulatus.*

28. A method for producing a desired protein in a bacterial host cell, said method comprising the steps of:

transforming a bacterial host cell with a recombinant vector comprising a first nucleotide sequence comprising the sequence of SEQ ID No 3, and a further nucleotide sequence that codes for said desired protein, wherein said further nucleotide sequence is operably linked in frame to said first nucleotide sequence; and culturing said transformed host cell in a suitable medium under conditions allowing expression of said desired protein.

29. The method according to claim 28, wherein the method further comprises the step of recovering the expressed protein or peptide from the medium.

30. The method according to claim 28, wherein the host cell is *M. capsulatus*.

31. The method according to claim 30, wherein the desired expressed protein is a drug.

32. The method according to claim 31, wherein the drug is extracted from the host cell, or used together with the host cell for the manufacturing of a vaccine.

33. The method according to claim 31, wherein the vaccine is for oral administration.

34. The method of claim 28, wherein the desired protein is a fusion protein containing a protein or peptide sequence encoded by a nucleotide sequence comprising the SEQ ID NO 3, and a further desired protein or peptide.

35. The bacterial host cell according to claim 26, wherein the recombinant vector codes for a protein which is expressed in the membrane.

36. The bacterial host cell according to claim 26, wherein the recombinant vector codes for a protein which is expressed on the surface of the outer membrane.

37. The bacterial host cell according to claim 35, wherein the bacterial cell is *M. capsulatus*.

38. The bacterial host cell according to claim 36, wherein the bacterial cell is *M. capsulatus*.

* * * * *